United States Patent [19]

Terada et al.

[11] Patent Number: 5,254,249

[45] Date of Patent: Oct. 19, 1993

[54] ANTI-THROMBOGENIC BLOOD TREATING SYSTEM

[75] Inventors: Ryozo Terada, Kanagawa; Kazumi Tanaka, Shiga; Tetsunosuke Kunitomo, Kanagawa, all of Japan

[73] Assignee: Toray Industries, Inc., Japan

[21] Appl. No.: 623,458

[22] PCT Filed: Apr. 25, 1990

[86] PCT No.: PCT/JP90/00536

§ 371 Date: Feb. 11, 1991

§ 102(e) Date: Feb. 11, 1991

[87] PCT Pub. No.: WO90/12607

PCT Pub. Date: Nov. 1, 1990

[30] Foreign Application Priority Data

Apr. 25, 1989 [JP] Japan .................... 1-106196

[51] Int. Cl.$^5$ .......................................... B01D 63/02
[52] U.S. Cl. ............................ 210/321.62; 210/321.8;
210/500.23; 210/500.24; 210/500.36; 422/44;
604/4; 604/5
[58] Field of Search ...................... 210/321.62, 321.79,
210/321.8, 321.81, 321.88, 321.89, 321.9,
500.23, 500.24, 500.36, 541; 604/4–6, 411;
422/44

[56] References Cited

U.S. PATENT DOCUMENTS

| | | | |
|---|---|---|---|
| 3,673,612 | 7/1972 | Merrill et al. ................. | 210/321.62 |
| 3,844,989 | 10/1974 | Harumiya et al. . | |
| 4,269,712 | 5/1981 | Hornby et al. ................. | 210/321.8 |
| 4,424,311 | 1/1984 | Nagaoka et al. ............... | 525/303 |
| 4,425,234 | 1/1984 | Reitz ............................. | 210/321.8 |
| 4,812,269 | 3/1989 | Harttig et al. ................. | 210/500.23 |
| 4,871,357 | 10/1989 | Hsu et al. ..................... | 604/269 |
| 4,872,867 | 10/1989 | Joh ............................... | 604/269 |
| 4,888,109 | 12/1989 | Manohar ....................... | 210/321.62 |
| 4,906,465 | 3/1990 | Chaikof et al. ............... | 623/1 |
| 4,965,112 | 10/1990 | Brinkman et al. ............. | 604/269 |

FOREIGN PATENT DOCUMENTS

| | | |
|---|---|---|
| 0046828 | 3/1982 | European Pat. Off. . |
| 0068509 | 1/1983 | European Pat. Off. . |
| 0273700 | 7/1988 | European Pat. Off. . |
| 57-14358 | 1/1982 | Japan . |
| 605308 | 5/1982 | Japan . |
| 60-22901 | 2/1985 | Japan . |
| 63-130103 | 2/1988 | Japan . |
| 8602087 | 4/1986 | World Int. Prop. O. . |

OTHER PUBLICATIONS

"Development of a New Antithrombogenic Continuous Ultrafiltration System", M. Arakawa et al, *Artificial Organs*, vol. 15, No. 3, 1991, pp. 171–179.

"Heparinized Polymers as Thromboresistant Biomaterials", J. E. Wilson, *Polm.-Plast. Technol. Eng.*, 16(2), 1981, pp. 119–208.

*Primary Examiner*—Robert A. Dawson
*Assistant Examiner*—Sun Uk Kim
*Attorney, Agent, or Firm*—Austin R. Miller

[57] ABSTRACT

An anti-thrombogenic blood treating system, comprising selectively permeable hollow yarn membranes made of a composition containing a copolymer with polyethylene oxide component, and headers, catheters and circuits respectively covered on the blood contact surface with a heparinized hydrophilic copolymer containing vinyl chloride as a component monomer or a hydrophilic copolymer with polyethylene oxide component, in combination. All the blood contact surfaces are made anti-thrombogenic to allow, for the first time, the long-time extracorporeal circulation without intracorporeal administration of heparin.

3 Claims, 3 Drawing Sheets

ANTI-THROMBOGENIC BLOOD TREATING SYSTEM

DESCRIPTION

1. Technical Field

The present invention relates to a new anti-thrombogenic blood treating system combining medical materials excellent in anti-thrombogenic property, with an artificial kidney of selectively permeable hollow yarn membranes excellent in anti-thrombogenic property, contamination resistance and solute permeability.

2. Background Arts

In recent years, hemocathartic therapy using extra corporeal circulation for a relatively long time such as CAVH is practiced, and many anti-thrombogenic materials have been being developed as medical materials used for it. However, still now, an anticoagulant such as heparin is administered to the whole body to make the blood non-coagulable for preventing the thrombogenesis. The administration of heparin, etc. to the whole body has a large disadvantage that the danger of bleeding becomes considerably high, and so, there is not yet any system which allows safe extracorporeal circulation.

Japanese Patent Laid-Open No. 85-22901 proposes the use of a copolymer with polyethylene oxide component as a hydrophilic high polymer. Japanese Patent Laid-Open No. 82-14358 discloses a heparinized hydrophilic copolymer containing vinyl chloride as a main component monomer, and Japanese Patent Laid-Open No. 83-5320 discloses a graft vinyl chloride copolymer containing a polyethylene oxide component of 5 or more in polymerization degree, as a medical anti-thrombogenic material.

However, these prior arts are insufficient as a practical anti-thrombogenic blood treating system for extracorporeal circulation, even though the anti-thrombogenic property of each material is greatly improved. Thus, the use of an anticoagulant such as heparin has been inevitable in practical extracorporeal circulation.

In view of the disadvantage of the above mentioned prior arts, the object of the present invention is to provide a safe anti-thrombogenic extracorporeal circulation system which allows extracorporeal circulation without using any anticoagulant such as heparin.

DISCLOSURE OF THE INVENTION

The present invention is an anti-thrombogenic blood treating system, comprising selectively permeable hollow yarn membranes containing a copolymer with polyethylene oxide component, and headers, catheters and circuits respectively covered on the blood contact surface with a heparinized hydrophilic copolymer containing vinyl chloride as a component monomer or a hydrophilic copolymer with polyethylene oxide component, in combination.

The following numbers and letters, and their corresponding descriptions, have been selected for ease of understanding of the invention herein.

| | |
|---|---|
| 1, 1': | catheter tube |
| 2, 2': | threaded catheter connector |
| 3: | connector |
| 4, 4': | cap for fixing the threaded connector |
| 5, 5': | blood circuit |
| 6, 6': | blood collecting section |
| 7, 7': | connector |
| 8: | blood inlet port |
| 8': | blood outlet port |
| 9: | header on inlet side |
| 10, 10': | silicone packing |
| 11: | inside space |
| 12, 12': | sealing material |
| 13: | end face of hollow yarn membranes |
| 14, 14': | filtrate outlet |
| 15: | module case |
| 16: | hollow yarn |
| 17: | header on outlet side |
| 18: | transfusion circuit |
| a: | inlet of blood circuit |
| b: | outlet of blood circuit |
| c: | junction face between catheter tube and connector |
| d: | hydrophilic copolymer covering layer |
| e: | close contact portion between catheter connector and circuit connector |
| f: | covering film |
| g: | space inside hollow yarn |

BEST MODE FOR CARRYING OUT THE INVENTION

The selectively permeable hollow yarn membrane of the present invention must contain, at least as one component, a copolymer with polyethylene oxide component to give anti-thrombogenic property, preferably a copolymer consisting of a polymerizable monomer with a polyethylene oxide component of 5 or more in polymerization degree and a polymerizable carbon-carbon double bond in the molecule (constituent I) and a monomer with a polymerizable carbon-carbon double bond (constituent II).

The constituent I is, for example, acrylic or methacrylic ester represented by the following general formula (1):

(where n stands for 5 or more; $R_1$, a hydrogen atom or methyl group; $R_2$, a hydroxyl group, alkoxy group with 1 to 4 carbon atoms, or $OCH\phi_2$ ($\phi$ stands for a phenyl group)), or a vinyl monomer represented by the following general formula (2):

(where n stands for 5 or more; $R_1$, a hydrogen atom or methyl group).

The constituent II is a monomer containing a carbon-carbon double bond copolymerizable with the constituent I, and can be selected, for example, from acrylic acid, methacrylic acid, methyl acrylate, methyl methacrylate, dimethylaminoethyl methacrylate, acrylonitrile, methvinyl acetate, vinyl chloride, styrene, vinylidene chloride, 2-hydroxyethyl methacrylate, N-vinyl pyrrolidone, acrylamide, diacetoneacrylamide, ethylene, propylene and butadiene.

Especially methoxypolyethylene glycol monomethacrylate can be preferably used as the constituent I, and acrylonitrile or methyl methacrylate, as the constituent II.

The copolymer of the constituents I and II can have an optional style. In order that the selectively permeable hollow yarn membrane obtained may have such features as inhibition of deposition of various components and excellent material permeability, the polymer constituting the selectively permeable hollow yarn membranes must have the ingredient I contain at least 1 wt % or more of a polyethylene oxide of 5 or more in polymerization degree. A preferable content of the polyethylene oxide component is in a range from 3 to 90 wt %.

If the polymerization degree of the polyethylene oxide component is less than 5, the stability of spinning is insufficient, and the obtained membrane is too low in mechanical strength to use. A preferable polymerization degree of the polyethylene oxide component is in a range from 9 to 300, more preferably 20 to 100.

The headers, catheters and circuits used in the present invention are made of a usually used material such as a material mainly containing polyurethane (constituent 1) or a material mainly containing polyvinyl chloride (constituent 2).

The constituent 1 can be polyurethane, or a blend consisting of polyurethane and another polymer (e.g., polyvinyl chloride, polymethyl methacrylate or polydimethylailoxane, etc.), or a graft copolymer or block copolymer consisting of the respective components.

The constituent 2 can be polyvinyl chloride or a copolymer consisting of vinyl chloride and another vinyl monomer such as ethylene, vinyl acetate, vinylidene chloride, acrylonitrile or methacrylic derivative, or a blend of polyvinyl chloride or any of its copolymers and another polymer (e.g., polyurethane or polymethyl methacrylate, etc.), or soft polyvinyl chloride composition consisting of said polymer and a straight chain dibasic acid ester such as dioctyl phthalate or dioctyl acetate or a plasticizer such as a phosphoric ester.

It is preferable that the molded medical material is a composition containing 30 wt % or more of polyurethane (constituent 1) or polyvinyl chloride (constituent 2) in view of mechanical properties, moldability, etc.

The molded medical material composed of a compound represented by said constituent 1 or 2 must have a layer of a heparinized hydrophilic copolymer (A) containing vinyl chloride as a component monomer or a layer of a hydrophilic copolymer (B) containing polyethylene oxide component formed at least on its blood contact surface.

The layer of a heparinized hydrophilic copolymer containing vinyl chloride as a component monomer is obtained by heparinizing a copolymer consisting of vinyl chloride and a hydrophilic monomer.

The hydrophilic monomer is described below in more detail. It is a vinyl monomer which can be homopolymerized into a water soluble polymer, and can be typically selected from acrylamide, methacrylamide, their derivatives, N-vinylpyrrolidone, glycerol, methacrylic esters of polyethylene glycol or methoxypolyethylene glycol, vinyl acetate (which can be polymerized and hydrolyzed into water soluble polyvinyl alcohol), their copolymers, etc. Especially in order to let the polymer layer evenly contain heparin deep inside and not to allow heparin to be simply dissolved out even under physiologic conditions for preventing the change in blood properties and for maintaining anti-thrombogenic property for a long time, it is preferable that the hydrophilic monomer contains a monomer with a tertiary amino group or any of its quaternary salts at the side chain.

For example, it can be selected from acrylic acid derivatives and methacrylic acid derivatives represented by the following general formula:

(where $R_1$ stands for a hydrogen atom or methyl group; and $R_2$ and $R_3$, respectively independently, a methyl group or ethyl group; and n, 1 to 3), their quaternary salts, 2- or 4-vinylpyridine, their derivatives, and their quaternary salts.

The copolymer containing these components can have any optional style, such as random copolymer, graft copolymer or block copolymer, etc. However, in view of the adhesiveness to the base, the balance between anti-thrombogenic property and mechanical properties, etc., a graft copolymer with polyvinyl chloride as the trunk polymer can be preferably used.

The mixing ratio of vinyl chloride and a hydrophilic monomer should be 1/9 (hydrophilic monomer/vinyl chloride by weight) to 8/2, preferably 2/8 to 7/3 in view of adhesiveness to the base, heparin content after heparinization, etc. The copolymer layer is formed by applying the copolymer using a common solvent onto a base, and it is brought into contact with a heparin solution.

As for the method for applying the heparinized hydrophilic copolymer (A) containing vinyl chloride as a component monomer onto the molded medical material, said copolymer is applied using a common solvent onto the surface of a material mainly containing polyurethane and vinyl chloride, and dried, and this operation is repeated till the copolymer layer reaches a predetermined thickness. The common solvent for the base and copolymer can be selected, for example, from dimethylformamide, dimethylacetamide, N-methylpyrrolidone, tetrahydrofuran, dioxane and their mixed solvents. In view of easy molding, etc., a solvent of 30° to 80° C. in boiling point, for example, tetrahydrofuran is preferable.

For heparinization, the copolymer is immersed into a heparin aqueous solution containing 0.5 to 5 wt % of heparin preferably at 50° to 80° C. for several hours to 5 days. In this case, it is preferable that the heparin aqueous solution contains 0 to 0.3N sodium chloride.

After completion of heparinization, the material is dried in vacuum at room temperature for 1 to 3 days, and sterilized as predetermined, to complete the production of an anti-thrombogenic medical material.

The hydrophilic copolymer (B) with polyethylene oxide component is only required to contain polyethylene oxide component, but can be preferably a copolymer of 0.2 or more, more preferably 0.5 or more in relative viscosity consisting of 5 wt % or more of a constituent represented by (where $R_1$ stands for a hydrogen atom or methyl group; $R_2$, a hydrogen atom, methyl group or ethyl group; and n, an integer of 5 or more) (constituent a) and 95 wt % or less of a vinyl polymer constituent containing vinyl chloride component (constituent b). In this case, n is preferably 5 or more, more preferably 5 to 300, furthermore preferably 10 to 150, for achieving sufficient anti-thrombogenic property. The relative viscosity refers to a value obtained by measuring at 25° C. a solution with 1 g/100 ml of said polymer dissolved in N,N-dimethylformamide.

The hydrophilic copolymer (B) with polyethylene oxide can have an optional style, but a graft copolymer with the constituent a graft-copolymerized to the constituent b can be preferably used. In this case, the constituent a can be preferably selected, for example, from polyethylene glycol monoacrylate or methacrylate. The constituent b can be any vinyl polymer containing vinyl chloride component, and can be selected, for example, from vinyl chloride homopolymer, copolymer of vinyl chloride and vinyl acetate, ternary copolymer of vinyl chloride, vinyl acetate and ethylene. In the case of a copolymer, it is preferable that vinyl chloride component is contained by 10 wt % or more, for utilizing the many features of polyvinyl chloride.

For graft-copolymerizing the acrylic or methacrylic ester monomer a to the constituent b obtained above respectively, for example, the constituent a is thermally polymerized in the presence of the constituent b using a hydrogen-extracting type radical initiator such as benzoyl peroxide, for chain transfer, to obtain a graft polymer. However, photo graft polymerization in which the constituent a is graft-copolymerized to the constituent b by the radical produced by the photolysis of the photo functional group introduced into the constituent b is preferable because the quantity, structure, positions, etc. of active points can be specified and furthermore because a graft polymer high in grafting rate can be obtained.

The photo functional group is preferably an N,N-dialkyldithiocarbamate group, and especially diethyldithiocarbamate (DTC group) can be preferably used in view of easy introduction, stability of product, etc. For example, a polymer constituent containing vinyl chloride component and sodium diethyldithiocarbamate are mixed in N,N-dimethylformamide, and the mixture is heated to 50°-60° C., to easily obtain a photo functional trunk polymer b containing DTC groups.

The photo graft polymerization of the monomer a to the constituent b can be easily achieved by dissolving the constituent b into a solvent such as tetrahydrofuran, dimethylformamide or cyclohexanone, etc., and irradiating with light with wavelengths in the ultraviolet region using a high pressure mercury lamp, etc. in an inactive gas current.

The mixing ratio of the constituents a and b for the graft copolymer is optional. When the amount of the former is 5 wt % or more, the effect of copolymerization appears, and an amount of 10 wt % or more is more preferable. Within this range, a vinyl monomer (constituent c) copolymerizable with the constituent a can be further added.

The constituent c can be selected, for example, from methacrylic esters such as methyl methacrylate, ethyl methacrylate and 2-hydroxyethyl methacrylate, styrene and vinyl acetate.

The application of the hydrophilic copolymer (B) with polyethylene oxide component obtained as above, to the medical base mainly composed of polyurethane or vinyl chloride is executed as done for the heparinized hydrophilic copolymer (A) containing vinyl chloride as a component monomer.

In this system, for the members constituting the system other than the selectively permeable hollow yarn membranes, the hydrophilic polymer (A) or (B) can be selected for each member, but it is preferable to use either (A) or (B) only for all the members.

The thickness of the layer of the heparinized hydrophilic copolymer (A) containing vinyl chloride as a component monomer or the thickness of the layer of the hydrophilic copolymer (B) with polyethylene oxide component can be controlled by the concentration of the copolymer in the coating solution (preferably 1 to 50 wt %) and the number of coating times. The thickness is recommended to be 1 μm or more, preferably 5 μm or more, to exhibit the effective anti-thrombogenic property in the body for a long time, at least for one day or more.

It is preferable that the drying after coating is executed in air, nitrogen or argon atmosphere, and the drying temperature is dependent on the solvent used, being in a range from room temperature to 100° C.

The molded medical material coated with the copolymer layer is then subjected to extraction in water or methanol, etc. in a temperature range from room temperature to boiling point, for removing such impurities as residual solvent, unreactive monomers, catalyst and polymerization inhibitor. If molded soft polyvinyl chloride containing a plasticizer is used as the base, an extraction medium containing 50% or more of water, for example, water/methanol=2/1 (by volume) is preferable in view of the removal of said impurities and the prevention of plasticizer dissolution.

When a medium larger than methanol in affinity to polyvinyl chloride, for example, acetone is used as an organic solvent, a larger water content is more preferable, needless to say.

The hydrophilic copolymer (A) or (B) obtained like this is used to make the molded members anti-thrombogenic, without changing the form of the members, to provide an anti-thrombogenic blood treating system allowing extra corporeal circulation for a long time without use of heparin.

The present invention is described below in reference to the drawings. However, the present invention is not limited thereto or thereby.

Figure 1:
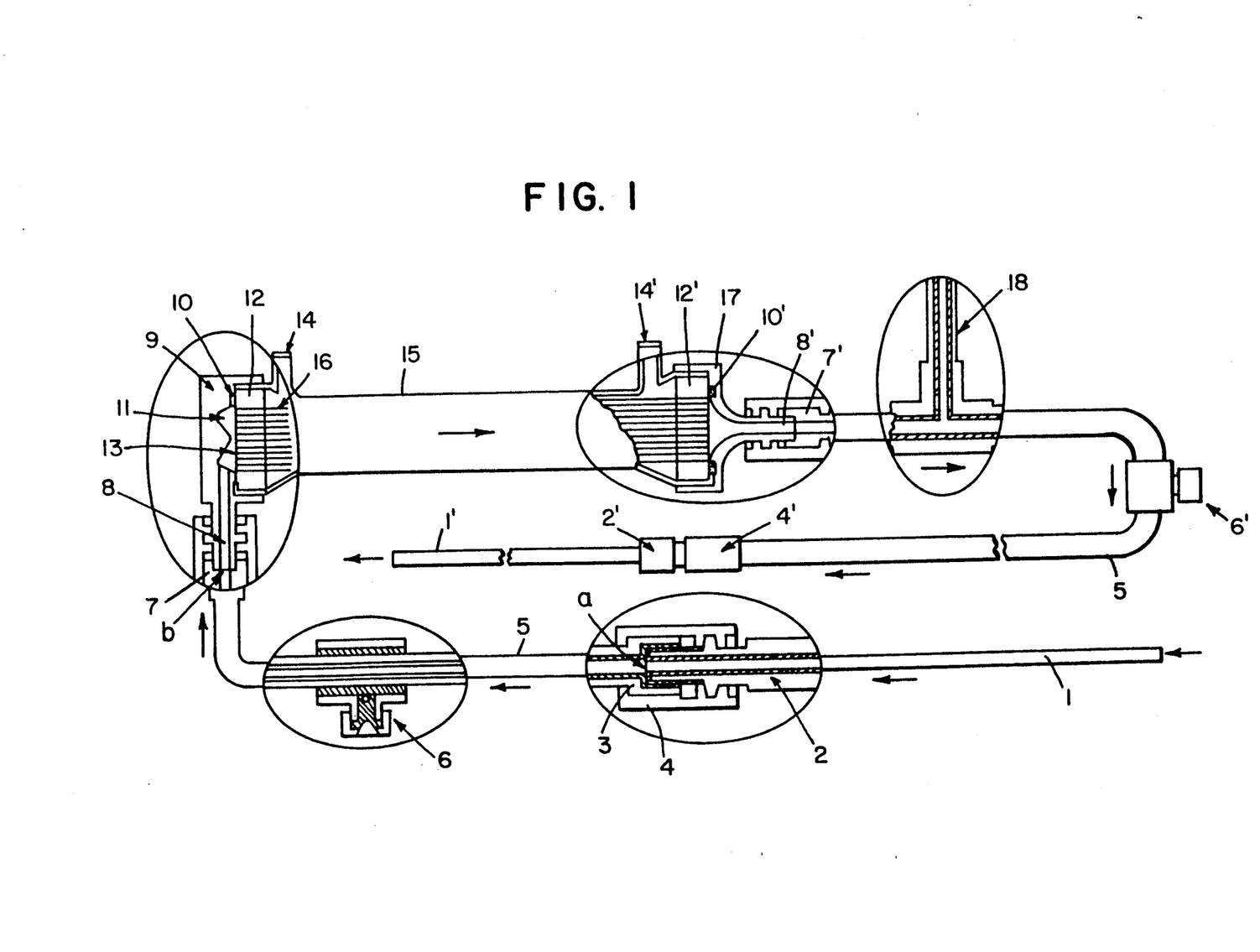
FIG. 1 is a general view showing the blood treating system of the present invention.

The anti-thrombogenic blood treating system is shown in FIG. 1.

The anti-thrombogenic blood treating system of the present invention consists mainly of catheters, circuits and a module.

The catheters of the system consist of molded medical catheter tubes 1 and 1' and catheter connectors 2 and 2' respectively mainly composed of polyvinyl chloride. At the junction between the catheter tube 1 and the connector 2 (in FIG. 2), the male connector 2 has the same internal space as the catheter tube 1, and is tapered from the junction face c with the catheter 1, to have the same internal space as a blood circuit 5. The taper angle should be 0 to 45 degrees, preferably 0 to 15 degrees. For perfect junction of the catheter connector 2, it is preferable to use a cap 4 for fixing the connector 2, and furthermore, it is preferable that the connector 2 and the connector cap 4 are threaded. The above description applies also to the other catheter tube 1' and connector 2'.

Figure 2:
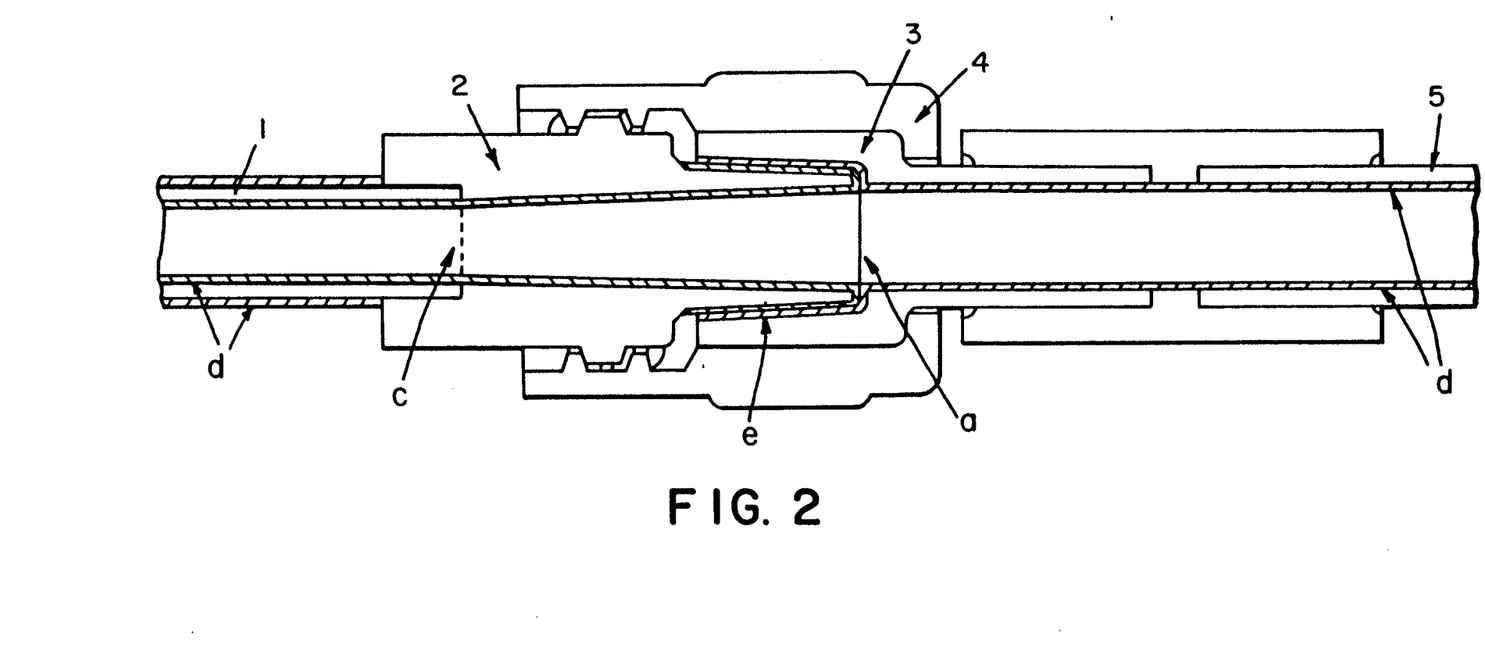
FIG. 2 is a sectional view showing the junction between a catheter tube and a connector.

Furthermore, the catheter tubes 1 and 1' are covered on the inside and outside surfaces with a continuous film d made of the hydrophilic high copolymer (A) or (B), and furthermore, the covering film d is continuous from the inside surface to the outside surface of the catheter connectors 2, to eliminate the discrete protrusions observed with the conventional catheter. Thus, anti-thrombogenic catheters with a blood contact surface free from the step at the junction are provided.

The circuits of the system are mainly composed of polyvinyl chloride, and include blood introducing circuit 3-7, blood returning circuit 3'-7', and a transfusion circuit 18. The blood introducing circuit is formed by using one tube 5 from the blood introduction inlet a to the outlet b, and the blood returning circuit is also formed by using one tube 5', to have a blood contact surface free from the protrusion formed for circuit joining. Furthermore, the blood introducing circuit and the blood returning circuit have female connectors 3 and 7 and 3' and 7' respectively for connection to the catheters and the headers of a module. The blood circuits and the connectors are covered on the inside surface with a continuous film d made of the heparinized hydrophilic copolymer (A) containing vinyl chloride as a component monomer or the hydrophilic copolymer (B) with polyethylene oxide component.

It is preferable that the blood circuits 5 and 5' are provided with blood collecting portions 6 and 6' and that the blood returning circuit 5' is provided with a transfusion circuit 18 covered with the hydrophilic copolymer (A) or (B).

Figure 3:
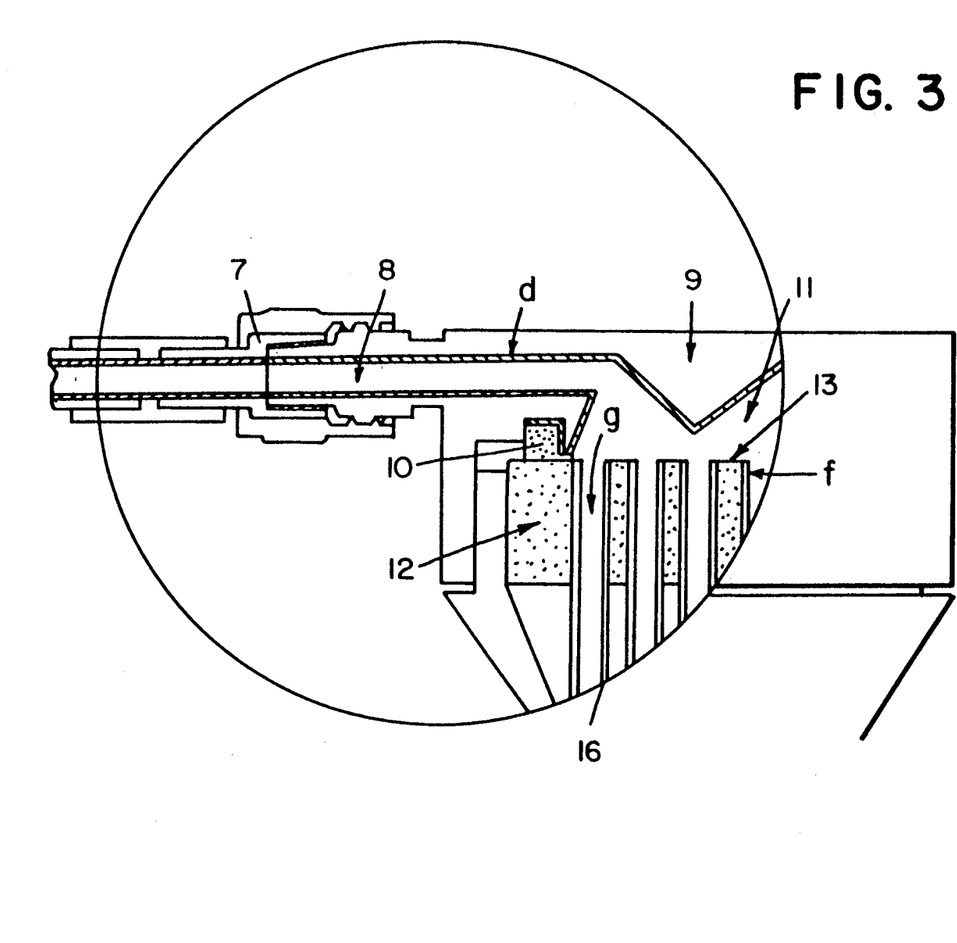
FIG. 3 is a sectional view showing the header the inlet side.

The module of the system is an artificial kidney module mainly composed of polyvinyl chloride and consists of a cross feed type header 9 on the blood inlet side and a conical header 17 on the blood outlet side or cross feed header 9 of the same type as that on the blood inlet side. The cross feed type header 9 has a blood inlet port 8 opened in the tangential direction of the inside space 11 on the inlet side, to prevent retention. The tangential direction is allowed to have a certain angle to the end face 13 of the hollow yarn membrane bundle. That is, the head can be opened at an angle of 0 to 50 degrees, preferably 0 to 30 degrees against the end face 13. Furthermore, the height of the inside space 11 on the inlet side is decided by the bore size of the blood inlet port 8.

The height of the inside space 11 on the inlet side should be preferably 1 to 5 times, more preferably 1 to 2 times the inner diameter of the blood inlet port 8. The inner diameter of the inside space should be preferably larger than the outer diameter of the hollow yarn membrane bundle by 0 to 2 mm, more preferably be equal to the outer diameter of the hollow yarn membrane bundle.

The blood inlet port 8 should be preferably in contact with the top of the inside space 11 on the inlet side of the cross feed type header 9, to ensure more uniform flow in the entire hollow yarn membranes. Furthermore, it is more preferable that the inside space has a conical protrusion at the center toward the open end face 13 of the hollow yarns.

Moreover, the header is covered on the inside surface with a continuous film d made of the heparinized hydrophilic copolymer (A) containing vinyl chloride as a component monomer or the hydrophilic copolymer (B) with polyethylene oxide component, as shown in FIG. 3, since the surface is the blood contact face. Thus, the blood can keep flowing in great contribution to the inhibition of thrombogenesis. Furthermore, it is preferable that as shown in FIG. 3, at the end face 13 on the inlet side of the hollow yarn membrane bundle for guiding into the spaces g inside the hollow yarns, and also at the end face 13' on the outlet side of the hollow yarn film bundle, a covering f with a uniform and free thickness is formed from each end face to the inside walls of the hollow yarn membranes at the joints of the outside walls of the hollow yarn membranes, by spraying an anti-thrombogenic material to the end face of the hollow yarn membranes, while blowing dry air or nitrogen from the other end face, to prevent the closing of hollow yarns. The anti-thrombogenic material can be any ordinary anti-thrombogenic material, for example, medical crosslinked silicone, or hydrophilic copolymer (A) or (B). The thickness should be preferably 0.2 to 5$\mu$, more preferably 0.2 to 2$\mu$. In addition, it is preferable that a covering film f made of the heparinized hydrophilic copolymer (A) containing vinyl chloride as a component monomer or the hydrophilic copolymer (B) with polyethylene oxide component is formed to reach from the anti-thrombogenic surfaces to the end faces of the hollow yarn membrane bundle.

In the present invention, it is preferable that the catheters, circuits and headers do not have any discrete protrusions on the inside surface at respective joints. That is, it is preferable that the respective joints between catheter tubes, connectors and blood circuits are free from any step, as shown in FIG. 2, and that the blood contact surfaces are covered d with the hydrophilic copolymer (A) or (B). That is, it is preferable that the catheter tubes 1 and 1' and the tapered catheter connectors 2 and 2' have the same radius at the respective joints, that the catheter connectors 2 and 2', the circuit connectors 3 and 3' and the blood circuits 5 and 5' have the same radius at the respective joints, and that the blood circuits 5 and 5' and the blood inlet ports 8 and blood outlet ports 8' of the headers have the same radius at the respective joints.

Furthermore, if the covering d made of the hydrophilic polymer (A) or (B) over the blood contact surface reaches the close contact portion e at the joint, as shown in FIG. 2, a safer anti-thrombogenic blood circuit can be provided.

These anti-thrombogenic catheters, circuits, headers and selectively permeable hollow yarn module can be combined to complete the anti-thrombogenic blood treating system of the present invention in which all the blood contact surfaces are covered with an anti-thrombogenic medical material.

The anti-thrombogenic property of these medical materials can be evaluated by various methods, for the respective applications such as in vitro, in vivo and ex vivo. As a result of these evaluations, the medical materials of the present invention have been found to be very excellent in anti-thrombogenic property.

EXAMPLES

The present invention is described below in reference to examples. The main members used had the following dimensions: Catheter tubes 1 and 1'... 2.7 mm in inner diameter and 150 mm in length. Blood circuits 5 and 5'... 4 mm in inner diameter and 60 cm in length. Catheter connectors 2 and 2'... 17 mm in length. Headers 9... 25 mm in inner diameter, 5.5 mm in the height of protrusion and 4 mm in the inner diameter of blood inlet port.

PRESENT INVENTION EXAMPLE 1

Thirty grams of photo graft active polyvinyl chloride (diethyldithiocarbamated polyvinyl chloride), 40 g of methoxypolyethylene glycol monomethacrylate of 20 to 23 in the polymerization degree of ethylene glycol portion, and 20 g of dimethylaminoethyl methacrylate were subjected to photo graft polymerization, using 1 liter of tetrahydrofuran as a solvent, by irradiating with a 100 W high pressure mercury lamp using an inside immersion type photo reactor for 6 hours, to obtain a graft polymer. The polyurethane catheters, polyvinyl chloride blood circuits (respectively including connectors) and polyvinyl chloride headers of the module (with selectively permeable hollow yarn membranes) respectively for the blood treating system of the present invention were coated with the polymer solution, using tetrahydrofuran as a solvent, on the surfaces to be in contact with the organisms and blood, as shown in FIGS. 1 to 3.

The coating was executed twice, and drying was executed at room temperature (22° C.) in nitrogen current. The thickness of the coating layer was 15 μm.

After completion of drying, the remaining monomers, solvent, etc. were extracted for 1 day, using a 60° C. mixed medium of water/methanol (2/1: by volume cc), and the respective members were immersed in 0.1N sodium chloride aqueous solution containing 2 wt % of heparin at 60° C. for 3 days for heparinization. Subsequently, unreactive heparin and residual salt were removed by ion exchange water, and the respective members were dried in vacuum at room temperature (22° C.) for two whole days and nights. The heparin content of the heparinized layer was measured by determining the sulfur atoms contained in heparin, by an X-ray microanalyzer, and found to be 21 wt %.

For the selectively permeable hollow yarn membranes of the module for the blood treating system, 154 parts by weight of acrylonitrile and 32 parts by weight of methoxy-polyethylene glycol monomethacrylate "M-900G" of 90 in the polymerization degree of polyethylene oxide component were added to 828 parts by weight of dimethyl sulfoxide (DMSO), and 1.4 parts by weight of 2,2'-azobis-2,4-dimethylvaleronitrile (hereinafter abbreviated as ADVN) were added. The mixture was polymerized at 41° C. for 8 hours, and the product was reprecipitated for purification by water/methanol, to obtain "M-900G" copolymerized polyacrylonitrile. The polyethylene oxide content in the copolymer was 30 wt %.

Seventy five point two grams of polyacrylonitrile was blended with 84.8 g of the copolymer, and the blend was dissolved into 840 g of DMSO. The mixture was stirred at 100° C. for 15 hours, to obtain a homogeneous transparent raw spinning solution. The viscosity of the raw spinning solution was 824 poises at 70° C.

The raw spinning solution was transfused into the raw solution storage tank of a spinning machine, and allowed to stand at 85° C. for 15 hours, for removing bubbles.

The spinning machine had a gear pump and a nozzle section in addition to the storage tank.

The spinning machine was mounted with a nozzle plate with a hollow tube in a circular orifice of 0.6 mm in outer diameter and 0.3 mm in inner diameter, and from the hollow tube, the raw spinning solution was spun into air at a rate of 1.2 g/min while nitrogen gas was fed from the hollow tube. The dry zone from the nozzle plate face was 7 mm long, and the spun solution was passed through 9% DMSO aqueous solution as a coagulating bath at 37° C., washed with water, thermally treated and wound at a rate of 20 m/min.

The selectively permeable hollow yarn membranes with polyethylene oxide component obtained like this were inserted into a plastic module, and a module for the blood treating system, of 300μ in the inner diameter of each hollow yarn, 140 mm in effective length and 0.25 m$^2$ in effective membrane area was prepared using a polyurethane potting agent.

Thirty six grams of polyvinyl chloride of 1100 in polymerization degree and 400 g of methoxypolyethylene glycol monomethacrylate (M-100G) with polyethylene glycol component of 100 in polymerization degree were dissolved into 1 liter of tetrahydrofuran, and the solution was irradiated with a high pressure mercury lamp in an external light source type photo polymerizer at 30° C. in argon current for 8 hours, to obtain a graft copolymer with M-100G grafted to polyvinyl chloride. It was reprecipitated in water/methanol, and extracted with methanol for purification, to remove the remaining monomers and impurities. It was then dried in air. The graft copolymer obtained like this was adjusted to a polymer concentration of 2 wt % by tetrahydrofuran, and the solution was stirred overnight at 40° C., centrifuged for purification, and formed into a film in nitrogen atmosphere at room temperature. The water content was 63%. The graft copolymer obtained like this was used to make the end faces of the module anti-thrombogenic. For the anti-thrombogenesis treatment, the graft copolymer solution was sprayed to an end face, and dry nitrogen or oxygen was blown in from the other side of the module, to secure the communicating portions of the hollow yarns. This treatment was applied also to the other end face of the module. Heparinized headers were fused to the end faces before the covering polymer solution became dry, to obtain the module for the blood treating system, which was anti-thrombogenic throughout from the inlet side header to the outlet side header.

To the module for the blood treating system obtained here, the heparinized catheters and circuits were connected, to form the blood treating system.

Seventeen adult dogs (about 12 kg) were intravenously injected with pentobarbital sodium, to be anesthetized, and subjected to arteriophlebotomy at the thigh using the blood treating system. The inlet catheter was inserted into the cut open artery and the outlet catheter, into the cut out vein respectively by about 10 cm. Immediately after insertion of the catheters, the circuits and module were connected, and one of the circuits was mounted with an ultrasonic blood flow meter, to initiate the extracorporeal circulation of blood. During extracorporeal circulation, heparin was not used, and the time taken till blood circulation became poor (80 ml/min or less in blood flow rate) due to the thrombogenesis of the entire system, thrombi, etc. was measured.

As soon as the blood circulation stopped, the inlet catheter was taken out of the artery, and the blood of the entire system was washed away by physiologic saline solution (80 ml/min).

Then, the thrombus deposition was observed, and portions free from thrombus deposition were sampled, to measure the amount of deposited protein by amino acid analysis.

As a result, it was found that out of 24 cases (17 dogs), 17 cases allowed the extracorporeal circulation for 6 hours or more (24 hours at the longest) without using heparin.

The amount of the blood ingredient (protein) deposited was 30 $\mu g/cm^2$ on the average as shown in Table 1. As for blood cells (platelets, red blood cells and white blood cells), only platelets were slightly deposited in the catheters, circuits and headers, to show excellent compatibility with the organism.

COMPARATIVE EXAMPLE 1

The polyurethane catheters and polyvinyl chloride circuits used in Present Invention Example 1, and a module composed of headers not coated with the heparinated hydrophilic copolymer containing vinyl chloride as a component monomer, and a hollow yarn membrane bundle with no hydrophilic copolymer contained in the polymethylmethacrylate polymer were combined, to obtain a blood treating system.

The blood treating system was used for extracorporeal circulation of blood with seven adult dogs (10 cases) as done in Present Invention Example 1. As a result, with all the 10 cases, thrombogenesis progressed as fast as to allow recognition by eyes, and the blood flow stopped in 15 to 60 minutes. Furthermore, also on the surfaces of the material free from thrombogenesis, the sticking and deposition of platelets, red blood cells and white blood cells were observed. The amount of protein deposited was 180 $\mu g/cm^2$.

TABLE 1

|  | Circulation time *1 min (n) | Amount of protein deposited *2 $\mu g/cm^2$ (n) |
|---|---|---|
| Present invention example 1 | 480 (7) | 30 ± 7.3 (3) |
| Comparative example 1 | 54 (10) | 180 ± 25.7 (3) |

*1 Measured by mounting an ultrasonic blood flow meter on one of the blood circuits.
*2 Measured in the portions free from thrombogensis.

PRESENT INVENTION EXAMPLE 2 AND COMPARATIVE EXAMPLE 2

The solution of the hydrophilic copolymer grafted with polyethylene oxide component of 100 in polymerization degree used for making the end faces of the module anti-thrombogenetic in Present Invention Example 1 was applied to the inside surface of a tube made of soft polyvinyl chloride (containing 40 parts of dioctyl phthalate as a plasticizer) of 4 mm in inner diameter, 6 mm in outer diameter and 900 mm in length. The coating was executed once, and drying was executed at room temperature (22° C.) in nitrogen current. The thickness of the coating layer was 10 $\mu m$.

After completion of drying, the remaining monomers, solvent, etc. were extracted for 1 day using a mixed solvent of water/methanol (2/1 by volume cc). Subsequently the remaining methanol was removed by ion exchange water, and the tube was dried in vacuum for two whole days and nights. Then, it was sterilized by ethylene oxide gas. The water content of the graft copolymer layer applied to the tube was 58%. A soft polyvinyl chloride tube not coated with the solution of the hydrophilic copolymer grafted with polyethylene oxide was used as a comparative example.

Five rabbits (about 3 kg) were anesthetized by administering pentobarbital sodium into the abdominal cavity, and subjected to arteriophlebotomy at the neck. Cannulae were inserted into the cut open portions, and tubes were connected, for extracorporeal circulation for 3 hours. The tubes were removed, and washed by physiologic saline solution, and the thrombus deposition on the layer of the hydrophilic copolymer with polyethylene oxide component was observed. Portions free from thrombus deposition were sampled, and the amount of protein deposited was measured by amino acid analysis.

The results are shown in Table 2. On the surfaces of the tubes with the layer of the hydrophilic copolymer with polyethylene oxide component of the present invention, few thrombi were formed, and the amount of protein deposited was as small as less than 1/15 of that on the surfaces of the tubes without the hydrophilic copolymer layer, to show excellent anti-thrombogenic property and compatibility with the organism. On the other hand, on the surfaces of the soft polyvinyl chloride tubes as Comparative Example 2, deposition of much plasma proteins was observed.

TABLE 2

|  | Existence of thrombi *1 | Amount of protein deposited *2 $\mu g/cm^2$ |
|---|---|---|
| Present invention example 2 | No | 1.6 ± 0.6 (n = 9) |
| Comparative example 2 | Yes | 27.3 ± 4.5 (n = 6) |

*1 Material surfaces were visually observed.
*2 Measured in the portions free from thrombogenesis.

PRESENT INVENTION EXAMPLES 3 AND 4

Catheters consisting of a medical polyurethane tube (thermoplastic polyether type polyurethane) of 2.8 mm in inner diameter, 3.8 mm in outer diameter and 200 mm in length and a connector made of unplasticized polyvinyl chloride (containing 14 parts of dioctyl phthalate as a plasticizer), and blood circuits (including the respective connectors) made of soft polyvinyl chloride (containing 40 parts of dioctyl phthalate as a plasticizer) were combined to prepare a combination free from discrete protrusions on the inside surface at joints.

The heparinized hydrophilic copolymer containing vinyl chloride or the hydrophilic copolymer with polyethylene oxide component used in Present Invention Example 1 was used for coating the combination of catheters and circuits as done in Present Invention Example 1.

Twelve rabbits (about 3 kg) were anaesthetized by administering pentobarbital sodium into the abdominal cavity, and subjected to arteriophlebotomy at the neck, and the catheters were inserted into the cut open portions. Then, the tubes were connected for extra-corporeal circulation for 3 hours. The catheters and the circuits were removed and washed by physiologic saline solution, to observe the thrombus deposition.

For the combination of catheters and circuits free from discrete protrusions coated with the heparinized hydrophilic copolymer containing vinyl chloride (Present Invention Example 3), and the combination of catheters and circuits free from discrete protrusions coated with the hydrophilic copolymer with polyethylene oxide component (Present Invention Example 4), the results as shown in Table 3 were obtained.

The combinations of catheters and circuits free from discrete protrusions coated with the heparinized hydrophilic copolymer containing vinyl chloride or with the hydrophilic copolymer with polyethylene oxide component kept thrombogenesis small, and a high blood flow rate could be maintained. From Present Invention Example 4, it is obvious that the hydrophilic copolymer with polyethylene oxide component shows excellent anti-thrombogenic property also in the blood treating system containing the module of the present invention.

TABLE 3

|  | Blood flow rate (ml/min) *1 3 hours later (n) | Existence of thrombi *2 |
| --- | --- | --- |
| Present invention example 3 | 120 ± 33 (3) | Few thrombi |
| Present invention example 4 | 130 ± 36 (3) | Few thrombi |

*1 Measured with an ultrasonic blood flow meter mounted on one of the blood circuits.
*2 Material surfaces were observed with eyes.

INDUSTRIAL APPLICABILITY

As described above, the present invention allows, for the first time, long-time extracorporeal circulation without intracorporeal administration of heparin, by making all the blood contact surfaces of a blood treating system anti-thrombogenic.

We claim:

1. An anti-thrombogenic blood treating system, comprising selectively permeable hollow yarn membranes made of a composition containing a copolymer consisting of a monomer with a polyethylene oxide component of 5 or more in polymerization degree and a polymerizable carbon-carbon double bond in the same molecule and a monomer with a polymerizable carbon-carbon double bond, and headers, catheters and circuits respectively covered on the blood contact surface with a heparinized hydrophilic copolymer containing vinyl chloride as a component monomer, in combination.

2. An anti-thrombogenic blood treating system, according to claim 1, wherein the inner surfaces at the joints between the headers, catheters and circuits are free from any discrete protrusions.

3. An anti-thrombogenic header comprising a layer of a heparinized hydrophilic copolymer containing vinyl chloride as a component monomer, said layer being formed on the inside, blood-contacting surface of said header, and wherein said header has a blood inlet port on an inlet side, and has an inner diameter, and has an inside space adjacent said blood inlet port, and has a bundle of hollow yarn membranes having an outer diameter connected to said inside space, and wherein said blood inlet port is arranged to open in a direction substantially tangential to the inside space of the header; wherein said inside space of said header has a height at the inlet side of about 1 to about 5 times the inner diameter of the opened blood inlet port; the inner diameter of the inside space is larger than the outer diameter of the hollow yarn membrane bundle by about 0 to about 2 mm; said blood inlet port is positioned in contact with the top of said inside space of said header; and said inside space has a substantially conical protrusion at its center extending toward opened end faces of the hollow yarn membranes.

* * * * *